(12) United States Patent
Dowling

(10) Patent No.: US 6,764,513 B1
(45) Date of Patent: Jul. 20, 2004

(54) TIBIA TETHER

(76) Inventor: Brian T. Dowling, 44 Butler Mill Rd., Elma, WA (US) 98541

( * ) Notice: Subject to any disclaimer, the term of this patent is extended or adjusted under 35 U.S.C. 154(b) by 93 days.

(21) Appl. No.: 10/035,723

(22) Filed: Nov. 7, 2001

(51) Int. Cl.$^7$ .................................................. A61F 2/08
(52) U.S. Cl. .................................................. 623/13.14
(58) Field of Search .......................... 623/13.11–13.2, 623/13 FOR; 60/72 FOR

(56) References Cited

U.S. PATENT DOCUMENTS

| | | |
|---|---|---|
| 3,953,896 A | 5/1976 | Treace |
| 4,246,660 A | 1/1981 | Wevers |
| 4,632,100 A | 12/1986 | Somers et al. |
| 4,744,793 A | 5/1988 | Parr et al. |
| 4,755,183 A | 7/1988 | Kenna |
| 4,773,910 A | 9/1988 | Chen et al. |
| 4,792,336 A | 12/1988 | Hlavacek et al. |
| 4,828,562 A | 5/1989 | Kenna |
| 4,927,421 A | 5/1990 | Goble et al. |
| 4,932,972 A | 6/1990 | Dunn et al. |
| 4,955,910 A | 9/1990 | Bolesky |
| 5,108,433 A | 4/1992 | May et al. |
| 5,383,878 A | 1/1995 | Roger et al. |
| 5,507,812 A | 4/1996 | Moore |
| 5,571,139 A | 11/1996 | Jenkins, Jr. |
| 5,628,766 A | 5/1997 | Johnson |
| 5,643,321 A | 7/1997 | McDevitt |
| 5,707,395 A | 1/1998 | Li |
| 5,916,557 A | 6/1999 | Berlowitz-Tarrant |
| 6,187,011 B1 | 2/2001 | Torrie |

FOREIGN PATENT DOCUMENTS

EP  0 317 408 A1 * 5/1989 ............. A61F/2/08

* cited by examiner

Primary Examiner—David H. Willse
(74) Attorney, Agent, or Firm—Sturm & Fix LLP

(57) ABSTRACT

A method for repairing a ligament using a crimp tube and a connector made of nylon or other suitable material. The method optionally utilizes a tensioner, a crimper, and a clamp. The method includes cutting open the skin and soft tissue surrounding the ligament, drilling holes through the bones surrounding the ligament, inserting a connector through the holes with the connector having a previously tightened knot at one end, placing a crimp tube around the connector at the opposite end of the connector from the knot, securing the connector in the tensioner, tightening the connector with the tensioner, crimping the crimp tube closed with the crimper against the connector, thereby securely coupling the bones together, and reattaching the skin and soft tissue.

4 Claims, 3 Drawing Sheets

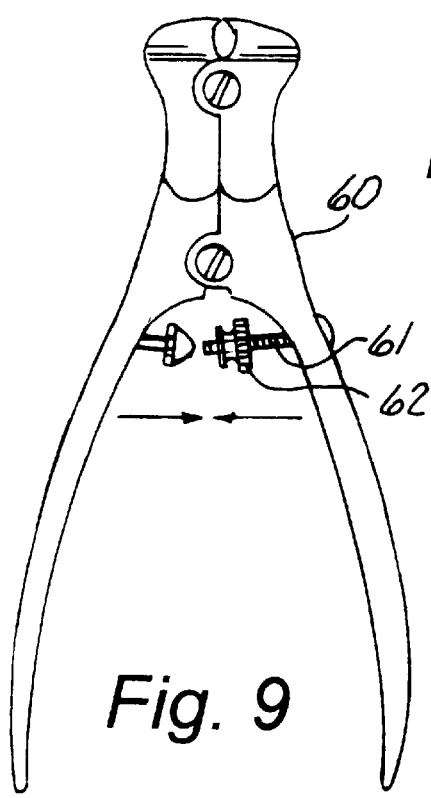
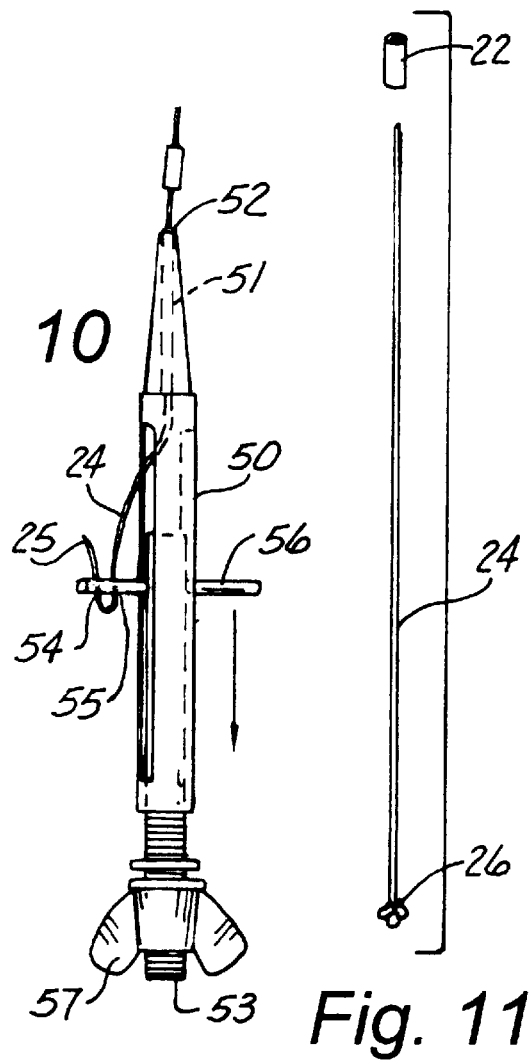

TIBIA TETHER

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO MICROFICHE APPENDIX

Not Applicable.

BACKGROUND OF THE INVENTION

1. Field of the Invention

This present invention relates to the field of ligament repair, and more particularly to ligament repair involving the use of a crimp tube and a connector.

2. Description of the Related Art

Ligament repair systems are well known in the art. Typical ligament repair systems use screws to anchor an artificial ligament in place. Typical ligament repair systems do not utilize a crimp tube and knot to secure an artificial ligament.

As can be seen by reference to the following U.S. Pat. Nos. 4,932,972, and 4,246,660, the prior art is replete with ligament repair systems. U.S. Pat. No. 4,932,972, titled "Prosthetic Ligament", is an invention designed to implant an artificial ligament through connecting bones, but the invention is distinguished from the present invention by the use of screws to secure the artificial ligament to the bones. In addition, U.S. Pat. No. 4,246,660 titled "Artificial Ligament", is also an invention designed to repair ligaments, but it also secures the artificial ligament to the bone with screws.

While all of the aforementioned prior art constructions are more than adequate for the basic purpose and function for which they have been specifically designed, they are uniformly deficient with respect to their failure to provide a simple, and efficient system for repairing ligaments. As the above described patents use a cumbersome method using screws to repair ligaments, a simpler method allowing quicker installation has been needed. The present invention utilizing a crimp tube and knot on either end of a connector supplies this needed method for increased efficiency.

BRIEF SUMMARY OF THE INVENTION

The invention is a method of repairing a ligament using a connector such as nylon as a replacement ligament, and fastening the connector with a knot on one end and a crimp tube on the other end. The method begins with the cutting open the skin and soft tissue surrounding the ligament. After the bones surrounding the ligament needing repair are exposed, holes are drilled through the bones to be connected by the ligament. Then the connector is inserted through the holes in the bones. A securely tightened knot previously formed at one end of the connector engages one of the holes firmly against the bone. A tensioning device is optionally used to tighten the connector within the crimp tube and the joint is checked for correct tension. Then the crimp tube is closed around the connector at the opposite end of the connector from the knot. The crimp tube is closed with a crimping device, thereby securely coupling the bones together. Extra connector material is cut off and, finally, the skin and soft tissue such as muscle are reattached.

BRIEF DESCRIPTION OF THE SEVERAL VIEWS OF THE DRAWING

These and other attributes of the invention will become more clear upon a thorough study of the following description of the best mode for carrying out the invention, particularly when reviewed in conjunction with the drawings, wherein:

FIG. 9 is a side elevational view of a surgical crimping device, modified with a cap nut on a threaded rod;

FIG. 10 is a side perspective view of a tensioning device with holes added to the top and crossbar of the tool; and FIG. 11 is a side elevational view of a connector and a crimp tube (shown without optional taper at end opposite knot).

DETAILED DESCRIPTION OF THE BEST MODE

Figure 1:
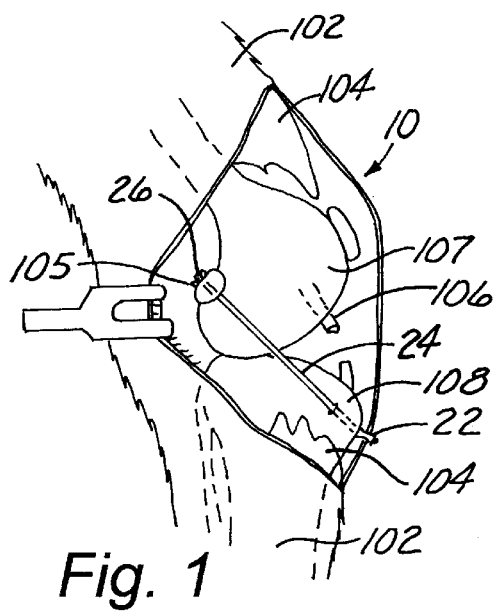
FIG. 1 is a perspective view of the present invention installed with skin and soft tissue pulled back.

As can be seen by reference to the drawings, and particular to FIG. 1, the ligament repair system that forms the basis of the present invention is designated generally by the reference number 10. A method of ligament repair 10 embodying the present invention is composed of repairing a ligament 106 using a crimp tube 22 and a connector 24 made of nylon or other suitable material.

Figure 2:
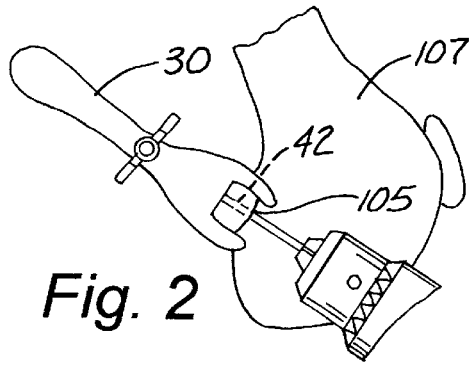
FIG. 2 is a perspective view of drilling through a bone with a clamp in place.
Figure 3:
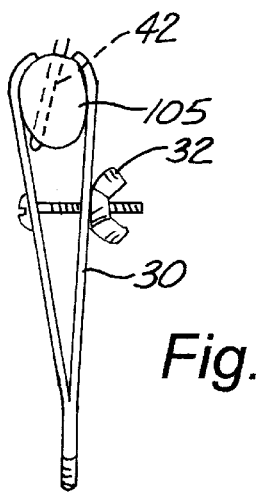
FIG. 3 is a side elevational view of a clamp gripping a first bone.
Figure 4:
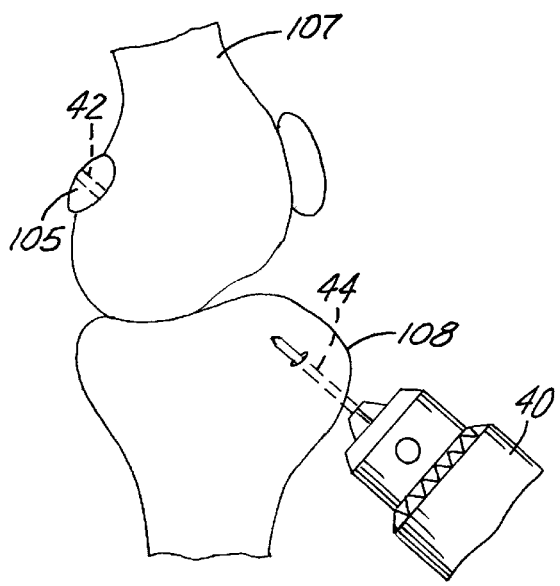
FIG. 4 is a perspective view of drilling through a second bone.

Initially, as seen in FIG. 1, the skin 102 and soft tissue 104 in the area of the ligament 106 needing repair is opened and the skin 102 is pulled back. In one embodiment, as shown in FIG. 2, the next step involves drilling through a first bone (for example, the lateral fabella) 105, next to the femur 107, in preparation for insertion of a connector 24 (FIG. 1). FIG. 2 shows an optional clamp 30 with tightenable wing nut 32 used to grip the lateral fabella 105 during drilling. FIG. 3 shows the drill hole 42 through the first bone 105 with the clamp 30 gripping the first bone 105. As shown in FIG. 4, after the hole 42 in the first bone 105 has been drilled, a hole 44 in the second bone 108 is drilled. FIG. 4 shows a hole 44 being drilled through a second bone 108.

Figure 5:
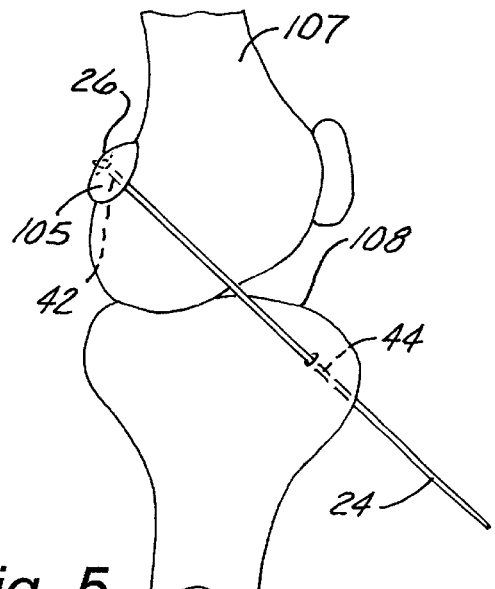
FIG. 5 is a perspective view of a connector inserted through a drilled hole through the first and second bones.
Figure 6:
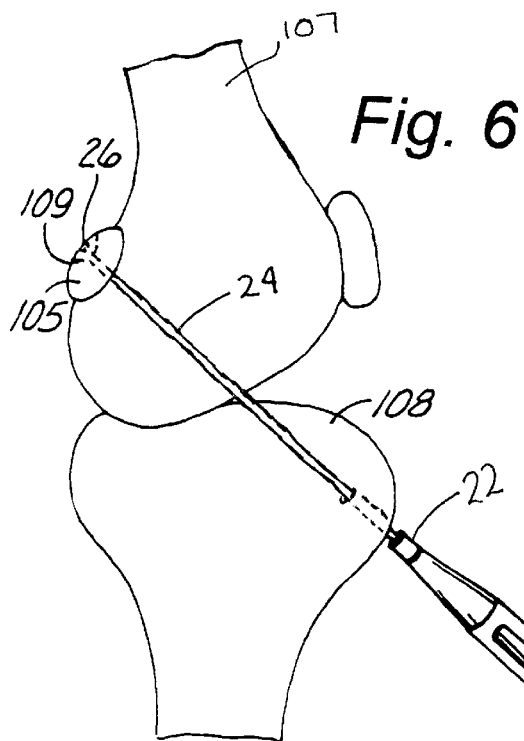
FIG. 6 is a perspective view of a tensioning device tightening a connector through a drilled hole through the bones, with placement of crimp tube.

As shown in FIG. 5, after the holes 42,44 are drilled through the bones 105,108, the connector 24 is inserted into the drilled holes 42,44 in the bones 105,108. The connector 24 is preferably made of semi-rigid material such as nylon that iscapable of being pushed into the holes 42,44. As shown in FIG. 6 and FIG. 11, a knot 26 is securely formed on one end of the connector 24. This is best done prior to sterilization due to the considerable force required to tighten the knot 26. In one embodiment of the invention, also shown in FIG. 6, a countersink opening 109 is drilled around the area of the knot 26, so that the knot 26 does not protrude from the bone 105. The positions of the knot 26 and crimp tube 22 can be reversed.

A tensioning device 50 tightens the connector 24 within the bones 105, 108. The tensioning device 50 can also be used for tightening cerciage wires. In one embodiment as shown in FIG. 10, the tensioning device 50 is a standard surgical tensioning device wherein the tensioning device 50 is modified such that a hole 51 is created through the top 52 of the device, as well as two holes 54, 55 in the crossbar 56. The tensioning device 50 operates by threading the connector 24 through the top 52 of the tensioning device 50, and inserting the end 25 of the connector 24 into the two holes 54, 55 in the crossbar 56. The connector 24 is tightened by turning the wingnut 57 on the bottom end 53 of the tensioning device 50. As the wingnut 57 is turned, the crossbar 56 is pulled downward as shown by the arrow in FIG. 10. The connector 24 is optionally tapered at the end opposite the knot 26, which allows for threading the connector 24 through tight spaces.

Figure 7:
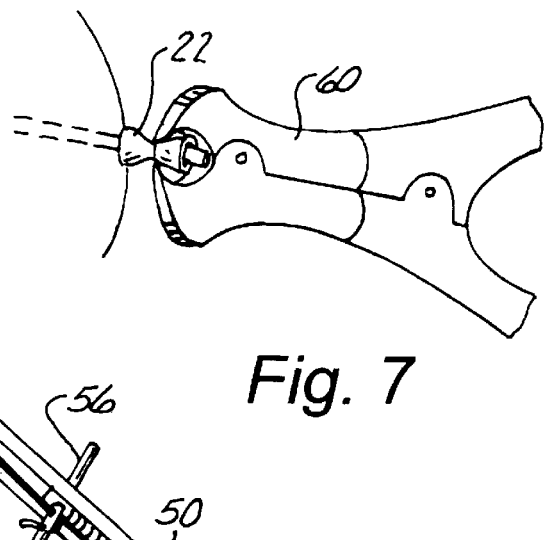
FIG. 7 is a perspective view of a crimping tool crimping closed a crimp tube surrounding a connector.
Figure 8:
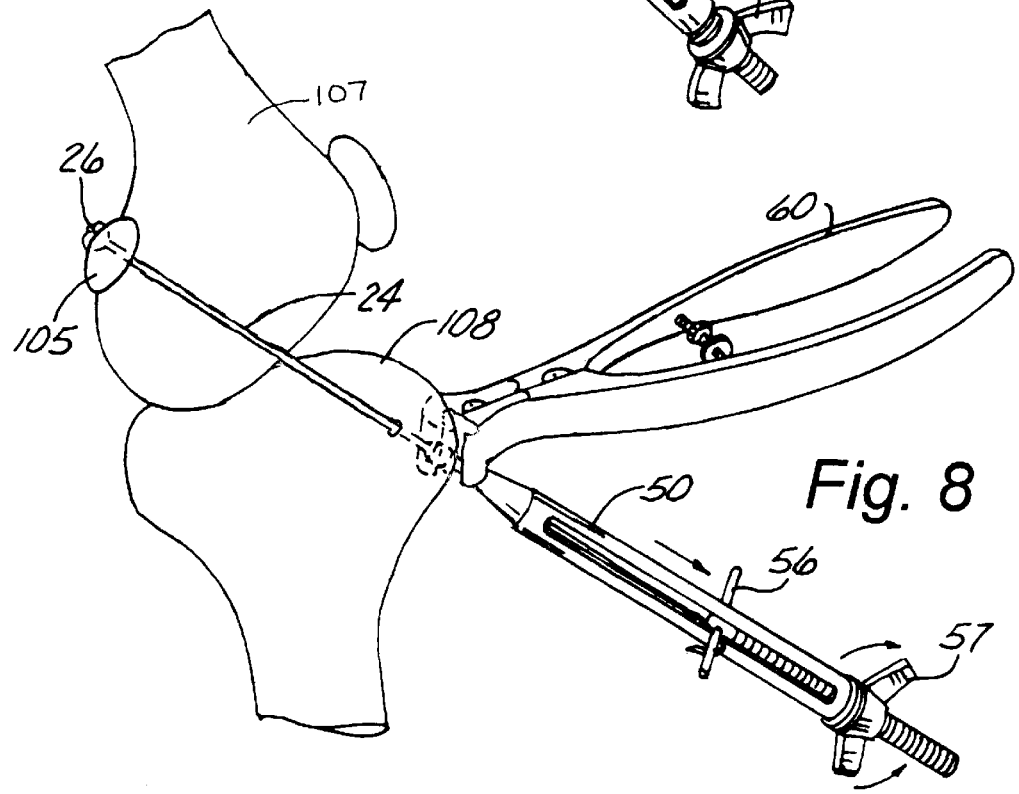
FIG. 8 is a perspective view of a tensioning device tightening a connector through a drilled hole through the bones, with the crimping tool in place crimping closed a crimp tube.

As shown in FIG. 7, after the tensioning device 50 has precisely tightened the connector 24, and the joint connection of the first bone 105 and the second bone 108 has been checked for correct tension, a crimping device 60 is used to close the crimp tube 22 over the connector 24. FIG. 8 also shows the crimping device 60 in place to crimp closed the crimp tube 22. In one embodiment, as shown in FIG. 9, the crimping device 60 is a modified surgical pin cutter. A surgical pin cutter is modified by threading a rod 61 and adding a cap nut 62. This cap nut 62 permits micrometer adjustment of the crimping device 60 to allow crimping different tube/ligament sizes as well as still being used as a pin cutter.

Finally, the skin 102 and soft tissue 104 is replaced. The above described method 10 enables the replacement ligament 24 to be buried beneath the soft tissue such as muscle 104 such that there is a minimum of friction of the replacement ligament 24 against skin 102 and soft tissue 104.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

What is claimed is:

1. A method of repairing a ligament, the method comprising:

cutting open skin and soft tissue surrounding the ligament;

drilling holes through the bones connected by the ligament;

inserting a connector through the holes, with the connector having a securely tightened knot at one end, and optionally a taper at the other end;

placing a crimp tube around the connector at the opposite end of the connector from the knot;

tightening the connector between the knot and the crimp tube;

crimping the crimp tube closed against the connector, thereby securely coupling the bones together; and reattaching the skin and soft issue.

2. The method of claim 1, wherein a canine cruciate ligament is repaired, with the connector disposed through the canine lateral fabella aid tribal crest bones.

3. The method of claim 1, wherein a tensioning device is used to tighten the connector, and the tensioning device is modified to contain a hole through a top of the tensioning device whereby a connector is tightened through the hole, and two holes are disposed in a crossbar of the tensioning device for securing a connector end.

4. The method of claim 1, wherein a surgical pin cutting device is used to crimp the crimp tube, and the pin cutting device is modified to contain a threaded rod and cap nut placed between two handles of the device for micrometer adjustment of crimping, while retaining the ability to cut pins.

* * * * *